United States Patent [19]
Bell et al.

[11] Patent Number: 5,834,488
[45] Date of Patent: Nov. 10, 1998

[54] DIHYDROBENZO [B] INDENO [2, 1-D] THIOPHENE COMPOUNDS, INTERMEDIATES, PROCESSES, COMPOSITIONS AND METHODS

[75] Inventors: Michael Gregory Bell; Brian Stephen Muehl; Mark Alan Winter, all of Indianapolis, Ind.

[73] Assignee: Eli Lilly and Company, Indianapolis, Ind.

[21] Appl. No.: 933,414

[22] Filed: Sep. 19, 1997

[51] Int. Cl.$^6$ .......... A61K 31/445; C07D 213/04
[52] U.S. Cl. .......... 514/324; 514/212; 514/232.8; 514/422; 514/443; 540/596; 544/146; 546/202; 548/525
[58] Field of Search .......... 549/42; 546/202; 548/525; 544/146; 514/212, 324, 232.8, 443, 422; 540/590

[56] References Cited

U.S. PATENT DOCUMENTS

| | | | |
|---|---|---|---|
| 3,274,213 | 9/1966 | Lednicer et al. | 260/326.5 |
| 3,394,125 | 7/1968 | Crenshaw | 260/326.5 |
| 3,413,305 | 11/1968 | Crenshaw | 260/326.5 |
| 4,133,814 | 1/1979 | Jones et al. | 260/326 |
| 4,230,862 | 10/1980 | Suarez et al. | 546/237 |
| 4,358,593 | 11/1982 | Jones et al. | 546/202 |
| 4,380,635 | 4/1983 | Peters | 546/202 |
| 4,418,068 | 11/1983 | Jones et al. | 546/237 |
| 5,147,880 | 9/1992 | Jones et al. | 514/650 |
| 5,395,842 | 3/1995 | Labrie | 514/320 |
| 5,470,854 | 11/1995 | Angerer et al. | 514/233 |
| 5,472,962 | 12/1995 | Koizumi et al. | 514/233.5 |
| 5,484,795 | 1/1996 | Bryant et al. | 514/212 |

FOREIGN PATENT DOCUMENTS

| | | | |
|---|---|---|---|
| 278774 | 2/1970 | Austria | 549/42 |
| 062 503 | 10/1982 | European Pat. Off. | |
| WO 89/0289 | 4/1989 | WIPO | |
| WO 95/10513 | 4/1995 | WIPO | |

OTHER PUBLICATIONS

Crenshaw, R.R., et al., *J. Med. Chem.* 14(12):1185–1190 (1971).

Jones, C.D., et al, *J. Med. Chem.* 27: 1057–1066) 1984.

Jones, C.D., et al, *J. Med. Chem.* 35: 931–938 1992.

*Primary Examiner*—Bernard Dentz
*Attorney, Agent, or Firm*—Janelle D. Strode; David E. Boone

[57] ABSTRACT

The invention provides dihydrobenzo[b]indenothiophene compounds, intermediates, processes, formulations, and methods of inhibiting bone loss or bone resorption, particularly osteoporosis, cardiovascular-related pathological conditions including hyperlipidemia and related cardiovascular pathologies, and estrogen-dependent cancer.

18 Claims, No Drawings

DIHYDROBENZO [B] INDENO [2, 1-D] THIOPHENE COMPOUNDS, INTERMEDIATES, PROCESSES, COMPOSITIONS AND METHODS

BACKGROUND OF THE INVENTION

This application claims the benefit of U.S. Provisional Application No. 60/026,718, filed Sep. 26, 1996.

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients. Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is primarily the net resorption and loss of the trabeculae which leads to the failure and fracture of bone. In light of the loss of the trabeculae in the postmenopausal woman, it is not surprising that the most common fractures are those associated with bones which are highly dependent on trabecular support, for example, the vertebrae, the neck of the weight-bearing bones such as the femur and the forearm. Indeed, hip fracture, collies fractures, and vertebral crush fractures are hallmarks of postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

Estrogen dependent cancers are major diseases effecting both women and to a lesser extent men. Cancer cells of this type are dependent on a source of estrogen to maintain the orginal tumor as well as to proliferate and metasize to other locations. The most common forms of estrogen dependent cancer are breast and uterine carcinomas. Current chemeotherapy of these diseases relies primarily on the use of anti-estrogens, predominately tamoxifene. The use of tamoxifene, although efficaceous, is not without undesirable side-effects, for example, estrogen agonist properties, such as uterine hypertrophy and carcinogenic potential. Compounds of the current invention while showing the same or better potential for anti-cancer activity, also demonstrate a lower potential for estrogen agonist activity.

In response to the clear need for new pharmaceutical agents which are capable of alleviating the symptoms of, inter alia, postmenopausal syndrome, the instant invention provides dihydrobenzo[b]indeno[2,1-d]thiophene compounds, pharmaceutical formulations thereof, and methods of using such compounds for the treatment of postmenopausal syndrome and other estrogen-related pathological conditions.

SUMMARY OF THE INVENTION

The instant invention relates to compounds of formula I:

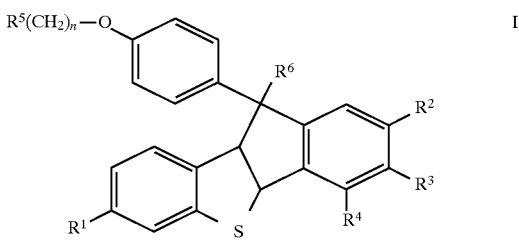

wherein:

$R^1$ is —H, —OH, —X, where —X is a halogen, —O($C_1$-$C_4$ alkyl), —OCO($C_1$-$C_6$ alkyl), —OCO(O) ($C_1$-$C_6$ alkyl), —OCOAr, —OCO(O)Ar where Ar is phenyl or substituted phenyl, or —OSO$_2$($C_4$-$C_6$ alkyl);

$R^2$, $R^3$, and $R^4$ are independently —H, —OH, —X, where —X is a halogen, —O($C_1$-$C_4$ alkyl), —OCO($C_1$-$C_6$ alkyl), —OCO(O) ($C_1$-$C_6$ alkyl), —OCOAr, —OCO(O)Ar where Ar is phenyl or substituted phenyl, or —OSO$_2$($C_4$-$C_6$ alkyl);

n is 2 or 3;

$R^5$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; and $R^6$ is —H, —OH, —X, where —X is a halogen, —CN, —NH$_2$, —NHR$^8$, —NR$^8$R$^9$, where R$^8$ and R$^9$ are both independently C$_1$–C$_6$ alkyl, or C$_1$–C$_6$ alkyl;

or a pharmaceutically acceptable salt or solvate thereof.

The instant invention also relates to compounds of formula III which are useful as intermediates for the synthesis of compounds of formula I:

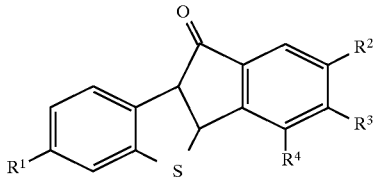

wherein R$^1$, R$^2$, R$^3$, and R$^4$ are as previously defined.

The instant invention further provides pharmaceutical formulations containing compounds of formula I, and the use of said compounds and/or formulations at least for the inhibition of bone loss or bone resorption, particularly osteoporosis, cardiovascular-related pathological conditions including hyperlipidemia, and estrogen-dependent cancer.

DETAILED DESCRIPTION OF THE INVENTION

General terms used in the description of compounds herein described bear their usual meanings. For example, "C$_1$–C$_6$ alkyl" refers to straight or branched aliphatic chains of 1 to 6 carbon atoms including methyl, ethyl, propyl, isopropyl, butyl, n-butyl, pentyl, isopentyl, hexyl, isohexyl, and the like. Similarly, the term "—OC$_1$–C$_4$ alkyl" represents a C$_1$–C$_4$ alkyl group attached through an oxygen such as, for example, methoxy, ethoxy, n-propoxy, isopropoxy, and the like. Of these C$_1$–C$_4$ alkoxy groups, methoxy is highly preferred.

The term "substituted phenyl" refers to a phenyl group having one or more substituents selected from the group consisting of C$_1$–C$_4$ alkyl, —OC$_1$–C$_4$ alkyl, hydroxy, nitro, chloro, fluoro, or tri(chloro or fluoro)methyl, and the like.

The term "hydroxy protecting group" contemplates numerous functionalities used in the literature to protect a hydroxy function during a chemical sequence, and which can be removed to yield the phenol. Included within this group would be acyls, mesylates, tosylates, benzyl, alkylsilyloxys, —C$_1$–C$_4$ alkyls, and the like. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965). Methods for removing preferred hydroxy protecting groups, particularly methyl, are essentially as described in the Examples infra.

The term "inhibit" includes its generally accepted meaning which includes prohibiting, preventing, restraining, and slowing, stopping, or reversing progression, severity, or ameliorating a resultant symptom or effect.

The term "solvate" represents an aggregate that comprises one or more molecules of the solute, such as a formula I compound, with one or more molecules of solvent.

Compounds of formula I include:

10-[4-[2-(1-Piperidinyl)ethoxy]phenyl]-3,7-dimethoxy dihydrobenzo[b]indeno[2,1-d]thiophene;

10-[4-[2-(1-Piperidinyl)ethoxy]phenyl]dihydrobenzo[b] indeno[2,1-d] thiophene;

10-[4-[2-(1-Piperidinyl)ethoxy]phenyl]-3,7-dihydroxy dihydrobenzo[b]indeno[2,1-d]thiophene;

10-[4-[2-(1-Piperidinyl)ethoxy]phenyl]-7-methoxy dihydrobenzo[b]indeno[2,1-d]thiophen-10-ol;

10-[4-[2-(1-Piperidinyl)ethoxy]phenyl]-2,7-dimethoxy dihydrobenzo[b]indeno[2,1-d]thiophen-10-ol;

10-[4-[2-(1-Piperidinyl)ethoxy]phenyl]-7-hydroxy dihydrobenzo[b]indeno[2,1-d]thiophen-10-ol;

10-[4-[2-(1-Piperidinyl)ethoxy]phenyl]-7-methoxy dihydrobenzo[b]indeno[2,1-d]thiophene;

10-[4-[2-(1-Piperidinyl)ethoxy]phenyl]-2,7-dimethoxydihydrobenzo[b]indeno[2,1-d]thiophene;

10-[4-[2-(1-Piperidinyl)ethoxy]phenyl]-7-hydroxy dihydrobenzo[b]indeno[2,1-d]thiophene hydrochloride, 10-[4-[2-(1-Pyrrolidinyl)ethoxy]phenyl]-3,7-dimethoxy dihydrobenzo[b]indeno[2,1-d]thiophene;

10-[4-[2-(1-Pyrrolidinyl)ethoxy]phenyl]dihydrobenzo[b] indeno[2,1-d] thiophene;

10-[4-[2-(1-Pyrrolidinyl)ethoxy]phenyl]-3,7-dihydroxy dihydrobenzo[b]indeno[2,1-d]thiophene;

10-[4-[2-(1-Pyrrolidinyl)ethoxy]phenyl]-7-methoxy dihydrobenzo[b]indeno[2,1-d]thiophen-10-ol;

10-[4-[2-(1-Pyrrolidinyl)ethoxy]phenyl]-2,7-dimethoxy dihydrobenzo[b]indeno[2,1-d]thiophen-10-ol;

10-[4-[2-(1-Pyrrolidinyl)ethoxy]phenyl]-7-hydroxy dihydrobenzo[b]indeno[2,1-d]thiophen-10-ol;

10-[4-[2-(1-Pyrrolidinyl)ethoxy]phenyl]-7-methoxy dihydrobenzo[b]indeno[2,1-d]thiophene;

10-[4-[2-(1-Pyrrolidinyl)ethoxy]phenyl]-2,7-dimethoxydihydrobenzo[b]indeno[2,1-d]thiophene;

10-[4-[2-(1-Pyrrolidinyl)ethoxy]phenyl]-7-hydroxy dihydrobenzo[b]indeno[2,1-d]thiophene hydrochloride, and the like.

The term "leaving group" means a chemical entity which is capable of being displaced by an amino function via an SN$_2$ reaction. Such reactions are well known in the art and such groups would include halogens, mesylates, tosylates, and the like. A preferred leaving group is bromo.

The compounds of formula I are derivatives of dihydrobenzo[b]indenothiophene, which is named and numbered according to the Ring Index, The American Chemical Society, as follows:

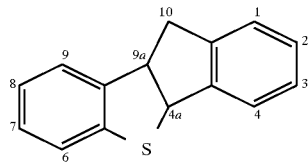

Several synthetic pathways are available for preparing intermediates and compounds of the instant invention. One synthetic route is illustrated in Scheme I, below. The starting material for the preparation of the compounds here is an indenobenzothiophene of formula XII. A representative synthesis is as provided in Preparation 4 below.

Scheme I

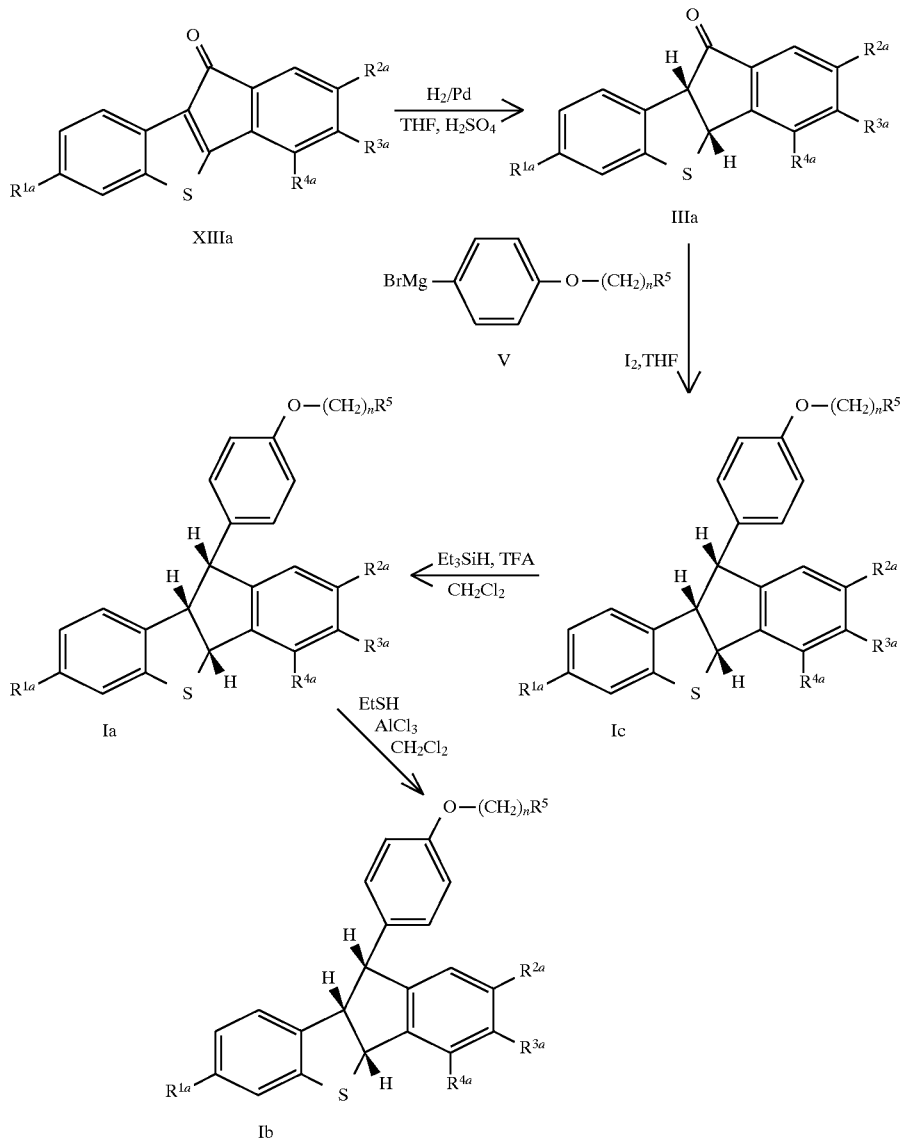

wherein n and $R^5$ are as defined above, $R^{1a}$ is —H or —$OR^7$, where $R^7$ is a hydroxy protecting group, $R^{2a}$, $R^{3a}$, and $R^{4a}$ are independently —H, —$OR^7$, where $R^7$ is a hydroxy protecting group, —F, —Cl, and $C_1$–$C_4$ alkyl.

An indenobenzothiophene of formula XIIIa is reduced to form the dihydroindenobenzothiophene of formula IIIa, typically in the presence of a suitable reducing catalyst such as for example palladium on carbon, in the presence of an acid, such as sulfuric acid, and a suitable solvent. This reaction is typically run at a variety of temperatures, usually in the range of from 25° C. to 150° C., and preferrably at about 60° C. The reaction is usually complete in one to 20 hours.

The second step in Scheme II continues with the reaction of IIIa with a Grignard reagent of formula V. The preferred bromo Grignard reagents may be prepared by reacting the bromo derivatives of a formula V compound with magnesium at ambient temperature in ether. The bromo precursors of formula V compounds are either commercially available or can be obtained from methods known in the art. Such compounds of formula V would include: 1-bromo-2-methoxybenzene, 1-bromo-3-methoxybenzene, 1-bromo-2-ethylbenzene, 1-bromo-3-methylbenzene, 1-bromo-2,4-difluorobenzene, 1-bromo-3-chlorobenzene, 1-bromo-2-chlorobenzene, 1-bromo-2-fluorobenzene, 2-bromo-4-fluoroanisole, 4-bromo-2-fluoroanisole, and the like. The addition reaction may be run at temperatures between 25° and 78° C. in inert solvents, such as THF, ethyl ether, dioxane, and the like. The reaction of V with IIIa yields compounds of formula Ic.

The carbinol of formula $I_c$ is reduced by treatment with a strong acid, which protonates the carbinol and forms the carbocation by elimination of water. Subsequently, the carbocation is reduced by a hydrogen donating agent. In the instant invention a preferred strong acid is trifluoroacetic acid, and the hydrogen donating source is a silane, particularly, trialkylsilane, and most preferred triethylsilane. This reaction may be run in $CH_2Cl_2$ at 0° C. and is complete typically within two hours.

A compound of formula Ia where $R^{1a}$ is methoxy may be selectively demethylated to form a compound of formula Ib by reacting said compound with ethanethiol and $AlCl_3$ in $CH_2Cl_2$.

An alternate means of reducing the indenobenzothiophene of formula XIIIa to provide the dihydroindenobenzothiophene of formula IIIa which employs lithium borohydride in THF is as provided in Scheme II below.

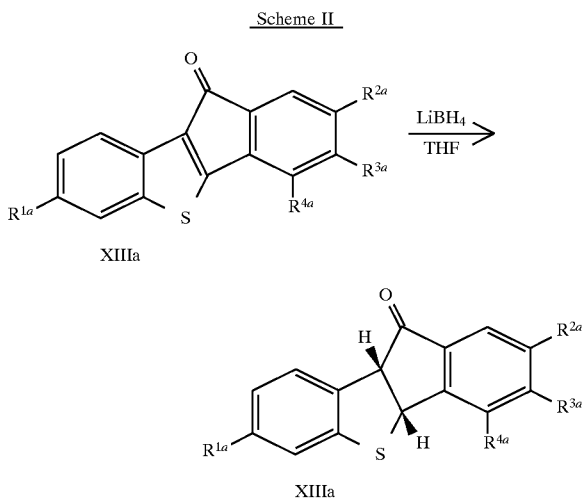

wherein $R^{1a}$, $R^{2a}$, $R^{3a}$ and $R^{4a}$ are as previously defined.

Another route in the synthesis of compounds of formula I employs the routes as illustrated by Schemes III, IV, V, and VI provided hereinbelow.

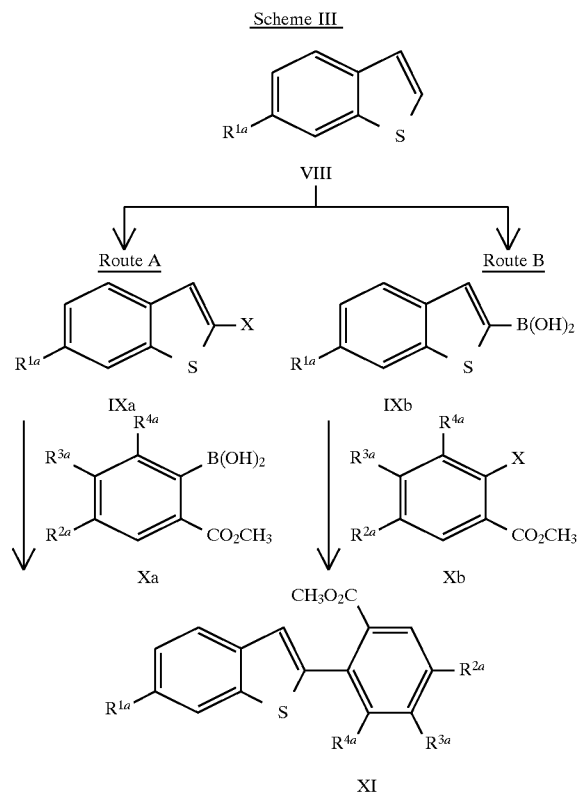

wherein $R^{1a}$, $R^{2a}$, $R^{3a}$, and $R^{4a}$ have their previous meanings; and X is a halogen.

The compounds of formula VIII may be prepared at least by the methods described in Jones et al., *J. Med. Chem.*, 27, 1057 (1984) and U.S. Pat. Nos. 4,133,814, 4,380,635, and 4,418,068, the disclosures of which are herein incorporated by reference. Compounds of formula VIII are arylated in the 2-position via Suzuki coupling [see, for example, Suzuki, A., *Pure and Appl. Chem.*, 6(2):213–222 (1994)]. Using one Suzuki coupling option, a formula VIII compound is selectively halogenated at the 2-position (VIIIa), and then coupled with an arylboronic acid compound of formula IXa (Scheme III, Route A) to provide intermediate compounds of formula XI.

Preferably, however, an arylboronic acid of formula IXb is formed from a compound of formula VIII, and then reacted with a halo-arene of formula Xb to give intermediates of formula XI (Scheme III, Route B). Such intermediates (XI) are useful for preparing pharmaceutically active compounds of the present invention (compounds of formula I).

The first step in Route A of Scheme III is the 2-position iodination or bromination of a formula VIII compound using standard procedures. Generally, a formula VIII compound is reacted with a slight excess of n-butyllithium in hexane, in an appropriate solvent and under an inert atmosphere such as nitrogen, followed by the dropwise addition of a slight excess of the desired halogenating agent in an appropriate solvent. Preferably the halogenating agent for this step is iodine. However, the use of bromine, such as, for example, N-bromosuccinimide, is sufficient.

Appropriate solvents include an inert solvent or mixture of solvents such as, for example, diethyl ether, dioxane, and tetrahydrofuran (THF). Of these, tetrahydrofuran, particularly anhydrous THF, is preferred.

The present selective, 2-position halogenation reaction is optionally run at a temperature from about −75° C. to about −85° C.

The product of the above reaction, a halo-arene of formula IXa, is then coupled with an arylboronic acid of formula Xa, via standard Suzuki coupling procedures, to provide compounds of formula XI. Compounds of formula Xa are derived from commercially available compounds via procedures well known to one of ordinary skill in the art (see, for example, March J.; and Suzuki, A., supra).

In the present coupling reaction, a slight excess of a formula Xa compound is reacted with each equivalent of a formula IXa compound in the presence of a palladium catalyst and an appropriate base in an inert solvent, such as toluene.

Although various palladium catalysts drive Suzuki coupling reactions, the catalyst selected is usually reaction-specific. The use of a triphenylphosphine palladium catalyst in the present reaction is a preferred catalyst.

Likewise, various bases may be used in the present coupling reaction. However, it is preferred to use triethylamine. The temperature employed in this step should be sufficient to effect completion of the coupling reaction. Typically, heating the reaction mixture to reflux for a period from about 2 to about 4 hours is adequate.

In Route B of Scheme III, a 2-position arylboronic acid of formula IXb is prepared using well known procedures. Generally, a compound of formula VIII is treated with a slight excess of n-butyllithium in hexanes, in an appropriate solvent, and under an inert atmosphere, such as nitrogen, following by the dropwise addition of an appropriate trialkylborate.

Appropriate solvents include an inert solvent or mixture of solvents such as, for example, diethyl ether, dioxane, and tetrahydrofuran (THF). THF, particularly anhydrous THF, is preferred. The preferred trialkylborate used in the present reaction is triisopropyl borate.

The product of this reaction, a compound of formula IXb, is then reacted with an aryl halide or aryl triflate of formula Xb, via standard Suzuki coupling procedures, to provide compounds of formula XI. The preferred reaction conditions for the present reaction are as described for the reaction of compounds of formula IXa and Xa, in Scheme III, which also provide compounds of formula XI.

Compounds of formula XI are then cyclized to provide the indenobenzothiophene intermediates of formula XIIIa, as provided below in Scheme III.

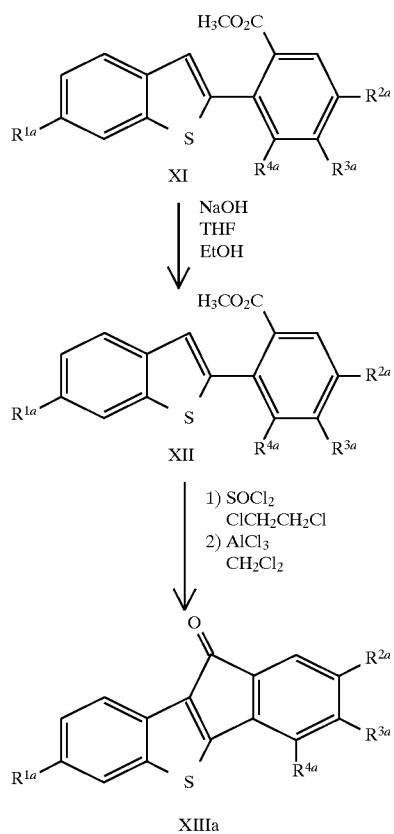

A compound of formula XI is demethylated to provide the carboxylic acid derivative of formula XII, typically in the presence of a strong base.

A compound of formula XII is then cyclized to provide the indenobenzothiophene intermediate of formula XIIIa. This cyclization is effected by Friedel-Crafts acylation, which has been previously described hereinabove.

An additional means of generating the compounds of formula XIIIa is provided in Scheme V below, wherein a compound of formula XIVa is also cyclized using Friedel-Crafts acylation to provide a compound of formula XIIIa.

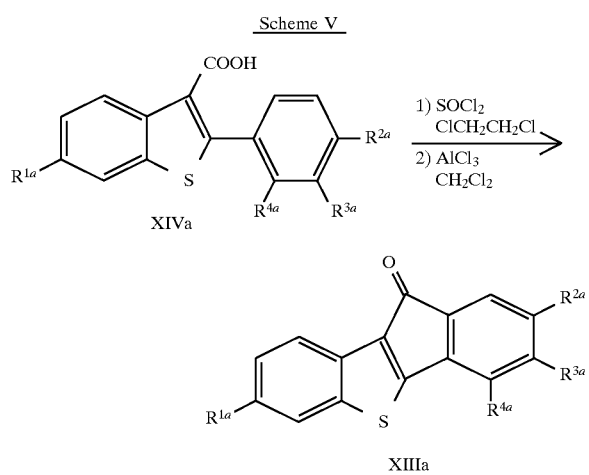

The compounds of formula XIVa may be conveniently prepared by the methods provided in Scheme VI, below.

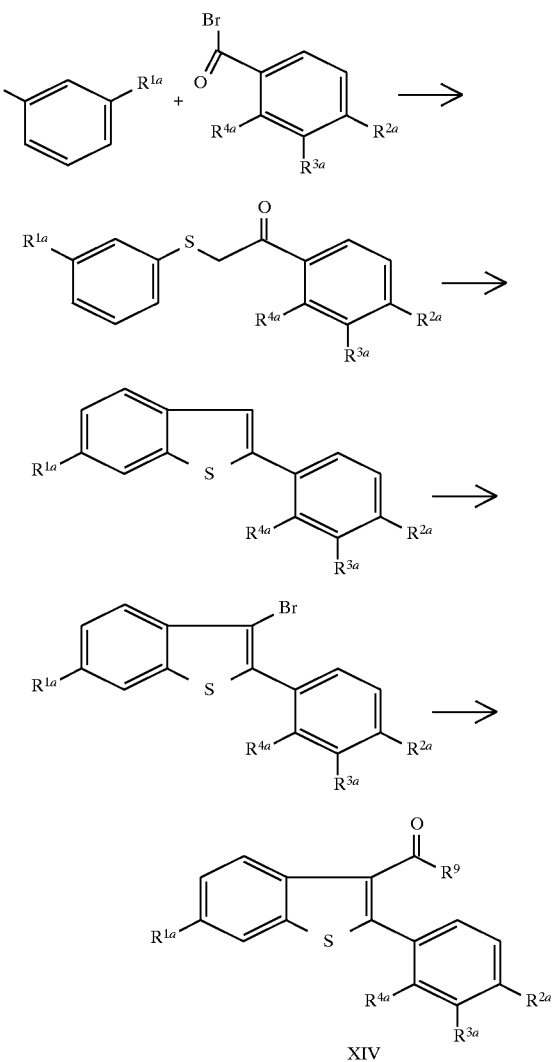

The compound of formula XIV, wherein $R^{1a}$, $R^{2a}$, $R^{3a}$, and $R^{4a}$ are as defined above, and $R^9$ is chloro, bromo, or hydroxyl, can be prepared by first reacting a 3-alkoxybenzenethiol with a phenacyl or 4'-alkoxyphenacyl bromide in the presence of a strong base. Suitable bases for this transformation include, potassium hydroxide and sodium hydroxide. The reaction is typically carried out in ethanol or a mixture of water and ethanol at a temperature of about 0° C. to about 50° C.

The next step is cyclization of the arylphenacylsulfide. The cyclization is conveniently carried out by heating the arylphenacylsulfide in polyphosphoric acid. The cyclization is typically carried out at a temperature of about 80° C. to about 120° C., preferably between 85° C. and 90° C. The intermediate benzothiophene is typically purified by recrystallization. For example, when $R^{1a}$ and $R^{2a}$ are methoxy, the intermediate benzothiophene compound may be recrystallized from ethyl acetate.

The intermediate benzothiophene compound is converted to a formula XIV compound by a sequence of steps comprising halogenation, lithiation, and carboxylation. First, the benzothiophene intermediate is converted to the corresponding 3-bromo analog by reaction with bromine in a halogenated hydrocarbon solvent. Suitable halogenated solvents for this reaction include carbon tetrachloride, chloroform, and methylene chloride; preferably a mixture of carbon tetrachloride and chloroform. This transformation is carried out at a temperature of about 25° C. to about 55° C. The intermediate 3-bromo benzothiophene compound is isolated using standard techniques, such as by recrystallization.

The 3-bromo intermediate is lithiated and carboxylated to prepare the formula XIV compound. The 3-bromo benzothiophene compound is reacted with an alkyl lithium, such as n-butyl lithium in a dry, polar organic solvent to produce the lithiated compound. Suitable solvents for this reaction include anhydrous diethyl ether, anhydrous tetrahydrofuran, and anhydrous dimethoxyethane. This reaction is typically run at the temperature of about −78° C. to about −50° C. The intermediate 3-lithiated benzothiophene compound is treated with carbon dioxide, either solid or gaseous, to produce the formula XIV compound wherein $R^9$ is —OH. This transformation is conveniently carried out in the same solvent as the lithiation reaction. The acid is typically isolated by acidification of the reaction mixture followed by recrystallization. For example, when $R^{1a}$ and $R^{2a}$ are methoxy and $R^9$ is hydroxy, the formula XIV compound can be recrystalized from absolute ethanol.

In an alternate synthetic scheme, benzo[b] indenothiophene intermediates of formula IIIa are employed in the synthesis of the compounds of formula I. This is illustrated in Scheme VII below.

Scheme VII

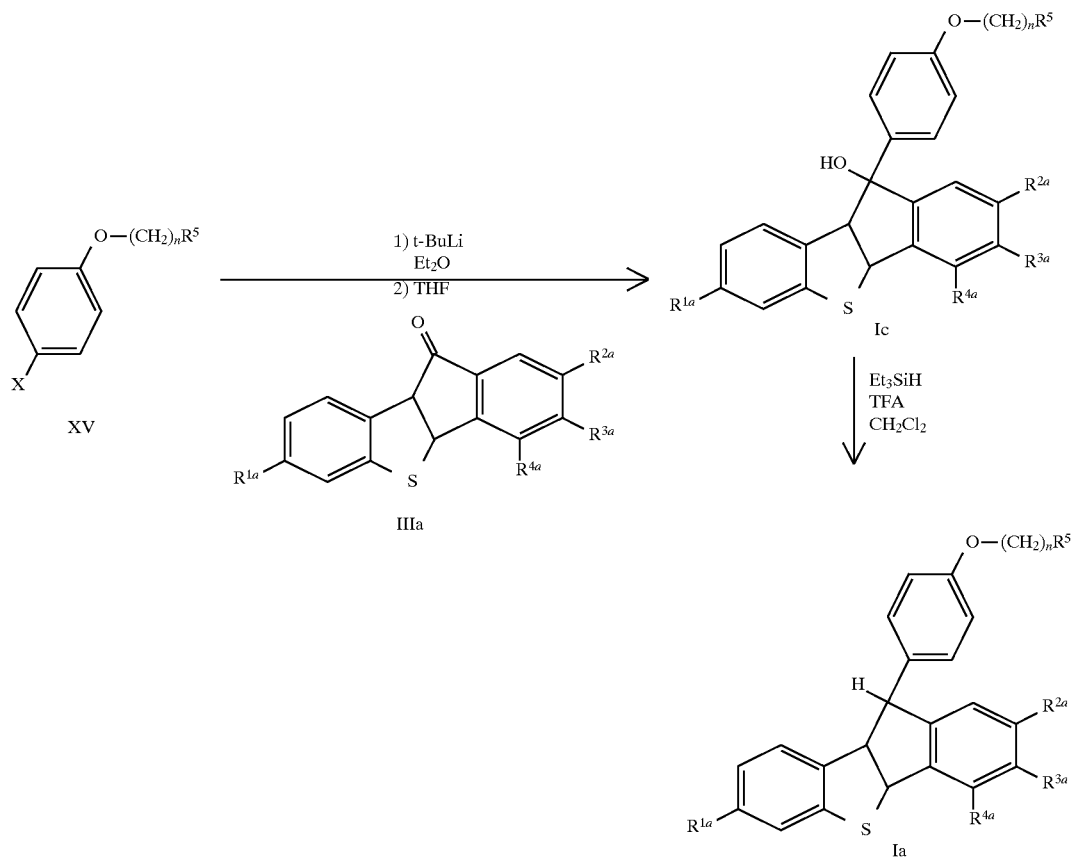

The aryl halide of formula XV is coupled with the dihydroindenobenzothiophene of formula IIIa to generate a compound of formula Ic. A compound of formula Ic may then be reduced to provide a compound of formula Ia. Deprotection of a compound of formula Ia results in a compound of formula Ib, one example of which is provided below in Scheme VIII.

Scheme VIII

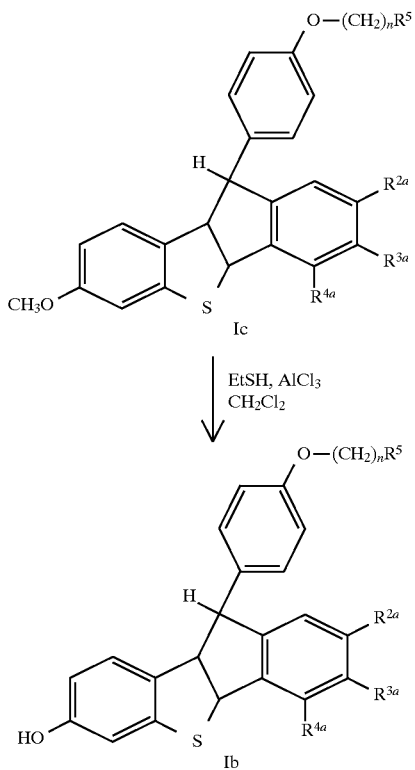

Compounds of formula Ia, Ib, and Ic are encompassed by formula I. Both isomers and mixtures of isomers generated at the 10-position are contemplated by, and within the scope of, the compounds of formula I.

Although the free-base form of formula I compounds can be used in the methods of the instant invention, it is preferred to prepare and use a pharmaceutically acceptable salt form. The term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means. The instant invention further provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the instant invention which is capable of inhibiting, alleviating, ameliorating, treating, or preventing further symptoms in mammals, including humans, suffering from bone loss or bone resorption, particularly osteoporosis, and cardiovascular-related pathological conditions including hyperlipidemia and related cardiovascular pathologies.

In the case of estrogen-dependent cancers, the term "effective amount" means the amount of compound of the instant invention which is capable of alleviating, ameliorating, inhibiting cancer growth, treating, or preventing the cancer and/or its symptoms in mammals, including humans.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissollution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to treat, inhibit, or prevent the symptoms and/ or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg, one to three times per day. Such dosages will be administered to a patient in need thereof for at least thirty days, and more typically for six months, or chronically.

The formulations which follow are given for purposes of illustration and are not intended to be limiting in any way. The total active ingredients in such formulations comprises from 0.1% to 99.9% by weight of the formulation. The term "active ingredient" means a compound of formula I.

Formulation 1: Gelatin Capsules

| Ingredient | Quantity (mg/capsule) |
|---|---|
| Active Ingredient | 0.1–1000 |
| Starch NF | 0–500 |
| Starch flowable powder | 0–500 |
| Silicone fluid 350 centistokes | 0–15 |

The ingredients are blended, passed through a No. 45 mesh U.S. sieve, and filled into hard gelatin capsules.

Formulation 2: Tablets

| Ingredient | Quantity (mg/tablet) |
|---|---|
| Active Ingredient | 2.5–1000 |
| Starch | 10–50 |
| Cellulose, microcrystalline | 10–20 |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50°–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

Formulation 3: Aerosol

| Ingredient | Weight % |
|---|---|
| Active Ingredient | 0.25 |
| Ethanol | 29.75 |
| Propellant 22 (Chlorodifluoromethane) | 70.00 |
| Total | 100.00 |

The active ingredient is mixed with ethanol and the mixture added to a portion of the propellant 22, cooled to 30° C. and transferred to a filling device. The required amount is then fed to a stainless steel container and diluted with the remainder of the propellant. The valve units are then fitted to the container.

Formulation 4: Suppositories

| Ingredient | Weight |
|---|---|
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5: Suspension
Suspensions each containing 0.1–1000 mg of a compound of formula I per 5 mL dose.

| Ingredient | Weight |
|---|---|
| Active Ingredient | 0.1–1000 mg |
| Sodium carboxymethyl cellulose | 50 mg |
| Syrup | 1.25 mL |
| Benzoic acid solution (0.1M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

The following Examples and Preparations are provided to better elucidate the practice of the instant invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

NMR data for the following Examples were generated on a GE 300 MHz NMR instrument, and anhydrous $CDCl_3$ was used as the solvent unless otherwise indicated. Field strength for $^{13}C$ NMR spectra was 75.5 MHz, unless otherwise indicated.

EXAMPLES

Preparation 1

7-Methoxy-4a,9a-dihydrobenzo[b]indeno[2,1-d]thiophen-10-one

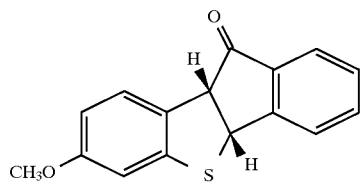

A solution of 3.5 g of 7-methoxybenzo[b]indeno[2,1-d]thiophene in 145 ml of tetrahydrofuran and 1.0 ml of concentrated sulfuric acid was treated with 5.3 g of 5% palladium on carbon under 60 psig hydrogen for two hours at 60° C. The solution was washed twice with brine, dried over sodium sulfate, filtered and concentrated to 2.5 g of a yellow oil. The oil was chromatographed over silca gel eluting with ethyl acetate and hexanes to give 890 mg of the titled compound as a yellow foam: MS m/z 268 (M$^+$); 300-MHz $^1$H NMR (CDCl$_3$) d 3.74 (s, 3H), 4.52 (d, J=8 Hz, 1H), 5.38 (d, J=8 Hz, 1H), 6.65 (d, J=2 Hz, 2H), 7.40–7.55 (m, 2H), 7.60–7.73 (m, 2H), 7.76 (d, J=8 Hz, 1H).

Preparation 2

6-Methoxy-2-[4-methoxy-2-methyl benzoate]benzo[b] thiophene

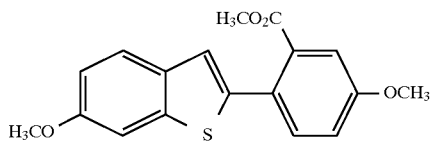

A mixture of 0.50 g of 6-methoxy-benzo[b]thiophen-2-yl boronic acid, 0.60 g of 5-methoxy-2-bromo-methyl benzoate, 0.017 g of palladium (II) acetate, 0.046 g of triphenylphosphine, and 0.87 ml of triethylamine in 25 ml dimethylformamide was heated at 100° C. for 18 hours. The reaction mixture was cooled to room temperature and evaporated. The resulting residue was dissolved in chloroform and water. The organic portion was separated from the mixture and the aqueous portion extracted with chloroform. The combined organic extracts were washed with saturated sodium bicarbonate and brine, dried (sodium sulfate), filtered, and evaporated. The resulting residue was chromatographed over silica gel eluting with 25% hexanes in toluene to provide 0.38 g of the title compound: MS m/z 329 (M$^+$+1); Anal. calcd for C$_{18}$H$_{16}$O$_4$S: C, 65.84; H, 4.91. Found: C, 65.84; H, 4.94.

Preparation 3

6-Methoxy-2-[4-methoxy-2-benzoic acid]benzo[b] thiophene

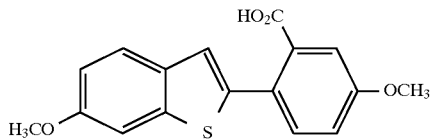

To a solution of 0.11 g of 6-methoxy-2-[4-methoxy-2-methylbenzoate]benzo[b]thiophene in 5 ml of tetrahydrofuran and 3 ml of ethanol at 22° C. was added 1.63 ml of 1N NaOH. The reaction mixture was stirred 18 hours at 22° C. and then heated at 50° C. for 5 hours. After cooling to room temperature, the reaction mixture was overwhelmed with water and extracted with chloroform. The aqueous portion was acidified with excess 1N HCl and extracted with ethyl acetate. The combined organic extracts were washed with brine, dried (sodium sulfate), filtered, and evaporated to give 0.09 g of the titled compound as an off-white crystalline solid: mp 201°–202° C.; MS m/z 314 (M$^+$).

Preparation 4
4A. 7-Methoxybenz[b]indeno[2,1-d]thiophen-10-one

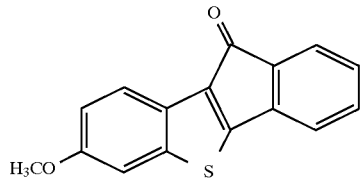

To a slurry of 15.0 g of 6-methoxy-3-carboxylic acid-2-phenylbenzo[b]thiophene and 4 drops of N,N-dimethylformamide in 300 ml of 1,2-dichloroethane at 22° C. was added 15.1 ml of thionyl chloride. The slurry was refluxed for 45 minutes, then evaporated to dryness. The solid was dissolved in 300 ml of dichloromethane and 15.5 g of aluminum chloride was added. The solution was refluxed for 3 hours then poured onto ice and extracted with three portions of chloroform. The chloroform extracts were washed with three portions of brine, dried (sodium sulfate) and evaporated to give 14.1 g of the title compound as a red solid: MS m/z 266 (M$^+$); 300-MHz $^1$H NMR (CDCl$_3$) d 3.89 (s, 3H), 7.05–7.40 (m, 5H), 7.45 (d, J=7 Hz, 1H), 8.00 (d, J=8 Hz, 1H); Anal. Calcd for C$_{16}$H$_{10}$O$_2$S: C, 72.16; H, 3.79. Found: C, 72.00; H, 3.74.

4B. 2,7-Dimethoxybenz[b]indeno[2,1-d]thiophen-10-one

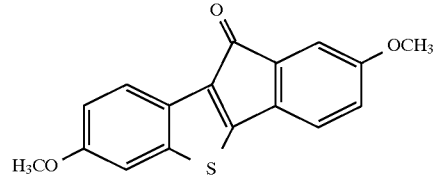

By following the procedure of part A, and substituting 6-methoxy-3-carboxylic acid-2-phenylbenzo[b]thiophene with 6-methoxy-3-carboxylic acid-2-[4-methoxyphenyl] benzo[b] thiophene; the title compound was obtained: MS m/z 296 (M$^+$). Anal. Calcd for C$_{17}$H$_{12}$O$_3$S: C, 68.90; H, 4.08; S, 10.82. Found: C, 69.12; H, 4.10; S, 10.68.

Preparation 5
2,7-Dimethoxy-4a,9a-dihydrobenzo[b]indeno[2,1-d] thiophen-10-one

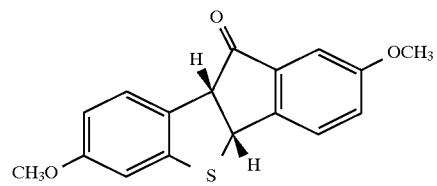

A mixture of 1.0 g of 2,7-dimethoxybenzo[b]indeno[2,1-d]thiophen-10-one and 80 mg of lithium borohydride in 30 ml of tetrahydrofuran was heated at reflux for 18 hours. The reaction was cooled to 22° C., quenched by addition of 200 ml of water and extracted with two portions of ethyl acetate. The organic extracts were washed with 1N sodium hydroxide, water and brine, dried (magnesium sulfate), filtered and evaporated. The resulting residue was chromatographed over silica gel eluting with ethyl acetate and toluene to give 0.20 g of the titled compound as a white solid: MS m/z 297 (M$^+$); IR (CHCl$_3$) 1710 cm$^{-1}$ (C=O); Anal. Calc'd for C$_{17}$H$_{14}$O$_3$S: C, 68.42; H, 4.74; N, none. Found: C, 68.51; H, 4.71; N, none.

Example 1
10-[4-[2-(1-Piperidyl)ethoxy]phenyl]-7-methoxy-4a,9a-dihydrobenzo[b]indeno[2,1-d]thiophen-10-ol

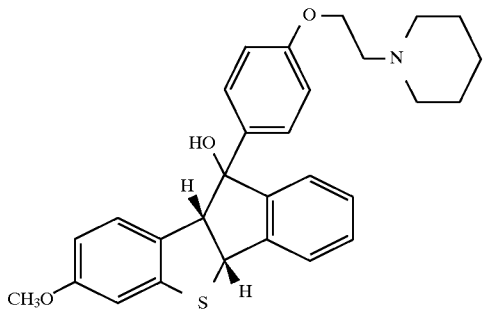

To a solution of 1.50 g of 7-methoxy-4a,9a-dihydrobenzo[b]indeno[2,1-d]thiophene in 20 ml of tetrahydrofuran at 0° C. was added 13.4 ml of 4-magnesium bromide-[2-(1-piperidyl)ethoxy] benzene in tetrahydrofuran (made by refluxing 2.78 g of the parent bromo in 10 ml of tetrahydrofuran with 0.72 g of magnesium powder for 1.5 h) at 0° C., and was warmed to room temperature over 2 h. The reaction was quenched with saturated aqueous sodium bicarbonate and 100 ml of ethyl acetate was added. The organics were separated, washed twice with brine, dried over sodium sulfate, filtered and concentrated to 2.77 g of a yellow oil. The oil was chromatographed over silica gel eluting with hexanes, ethyl acetate and methanol to yield 1.50 g of the titled compound as a yellow oil: MS m/z 474 (M+); 300-MHz $^1$H NMR (CDCl$_3$) d 1.40–1.52 (m, 2H), 1.52–1.70 (m, 4H), 2.34 (s, 1H), 2.45–2.60 (m, 4H), 2.75–2.85 (m, 2H), 3.80 (s, 3H), 4.05–4.10 (m, 2H), 4.34 (d, J=7 Hz, 1H), 5.65 (d, J=8 Hz, 1H), 6.60 (m, 1H), 6.71 (d, J=3 Hz, 1H), 6.85–6.96 (m, 4H), 7.14 (d, J=7 Hz, 1H), 7.22–7.48 (m, 4H).

Example 2
10-[4-[2-(1-Piperidyl)ethoxy]phenyl]-7-methoxy-4a,9a-dihydrobenzo[b]indeno[2,1-d]thiophene

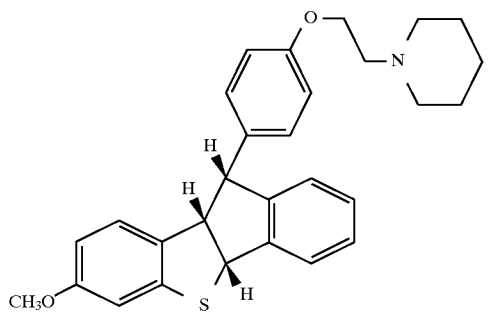

A solution of 0.96 g of triethylsilane in 24 ml of trifluoroacetic acid at 0° C. was quickly added to a solution of 1.43 g of 10-[4-[2-(1-piperidyl)ethoxy]phenyl]-7-methoxy-4a,9a-dihydrobenzo[b]indeno[2,1-d]thiophen-10-ol in 100 ml of dichloroethane at 0° C. The resulting solution was warmed to room temperature and 100 ml of water was added. The organic layer was separated, washed twice with saturated aqueous sodium bicarbonate, twice with brine, dried over sodium sulfate, filtered and concentrated to give 1.65 g of the titled compound as a brown oil: MS m/z 458 (M+); 300 MHz $^1$H NMR (CDCl$_3$) d 1.35–1.50 (m, 2H), 1.80–2.00 (m, 4H), 2.10–2.30 (m, 2H), 2.70–2.95 (m, 2H), 3.30–3.42 (m, 2H), 3.66 (s, 3H), 4.40–4.50 (m, 2H), 4.70 (d, J=9 Hz, 1H), 4.88 (d, J=9 Hz, 1H), 5.56 (d, J=7 Hz, 1H), 6.12 (d J=8 Hz, 1H), 6.19 (d, J=8 Hz, 1H), 6.52 (s, 1H), 6.64 (d, J=8 Hz, 2H), 6.86–7.00 (m, 3H), 7.23–7.35 (m, 2H), 7.30 (d, J=4 Hz, 1H).

Example 3
10-[4-[2-(1-Piperidyl)ethoxy]phenyl]-7-hydroxy-4a,9a-dihydrobenzo[b]indeno[2,1-d]thiophene

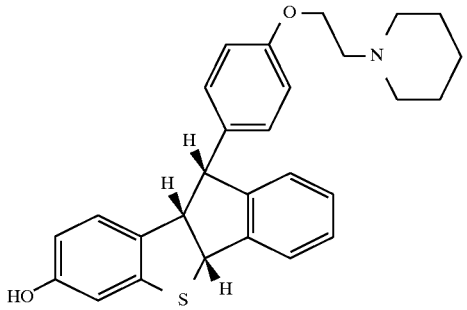

To a solution of 1.63 g of 10-[4-[2-(1-piperidyl) ethoxy] phenyl]-7-methoxy-4a,9a-dihydrobenzo[b]indeno[2,1-d]thiophene in 250 ml of dichloroethane was added 1.3 ml of ethanethiol and 2.4 g of aluminum chloride. The solution was stirred overnight at room temperature. The reaction mixture was quenched with saturated aqueous sodium bicarbonate and then 20 ml of methanol was added. The aqueous layer was extracted twice with chloroform. The combined organic layers were washed twice with brine, dried over sodium sulfate, filtered and concentrated to 1.24 g of a brown oil. The oil was chromatographed over silica gel eluting with methanol and chloroform to give 320 mg of the titled compound as a yellow foam: MS m/z 444 (M+); 300 MHz $^1$H NMR (CDCl$_3$) d 1.40–1.55 (m, 2H), 1.55–1.66 (m, 4H), 2.45–2.60 (m, 4H), 2.70–2.80 (m, 2H), 4.04 (t, J=6 Hz, 2H), 4.65 (d, J=9 Hz, 1H), 4.85 (d, J=9 Hz, 1H), 5.41 (d, J=9 Hz, 1H), 6.05 (ABq, J=6 Hz, Dn=19 Hz, 2H), 6.43 (s, 1H), 6.59 (d, J=8 Hz, 2H), 6.84 (d, J=8 Hz, 2H), 7.02 (d, J=8 Hz, 1H), 7.20–7.35 (m, 3H), 7.40 (d, J=7 Hz, 1H); Anal. Calc'd for $C_{28}H_{27}NO_3S$: C, 75.81; H, 6.59; N, 3.16. Found: C, 75.63; H, 6.44; N, 2.89.

Test Procedures

In the examples illustrating the methods, a postmenopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen Tissue Collection

After a one week acclimation period (therefore, two weeks post-OVX) daily dosing with test compound was initiated. 17a-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine: xylazine (2:1, V:V) mixture and a blood sample was collected by cardiac puncture. The animals were then sacrificed by asphyxiation with $CO_2$, the uterus was removed through a midline incision, and a wet uterine weight was determined.

Cholesterol Analysis

Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve.

Uterine Eosinophil Peroxidase (EPO) Assay

Uteri were kept at 40° C. until time of enzymatic analysis. The uteri were then homogenized in 50 volumes of 50 mM Tris buffer (pH-8.0) containing 0.005% Triton X-100. Upon addition of 0.01% hydrogen peroxide and 10 mM O-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound 17a-ethynyl estradiol was obtained from Sigma Chemical Co., St. Louis, Mo.

Influence of Formula I Compounds on Serum Cholesterol and Determination of Agonist/Non-Agonist Activity Data presented in Table 1 below show comparative results among ovariectomized rats, rats treated with 17a-ethynyl estradiol ($EE_2$; an orally available form of estrogen), and rats treated with certain compounds of the instant invention. Although $EE_2$ caused a decrease in serum cholesterol when orally administered at 0.1 mg/kg/day, it also exerted a stimulatory action on the uterus so that $EE_2$ uterine weight was substantially greater than the uterine weight of ovariectomized test animals. This uterine response to estrogen is well recognized in the art.

Not only did the compounds of the instant invention generally reduce serum cholesterol compared to the ovariectomized control animals, but uterine weight was only minimally increased to slightly decreased with the majority of the formula compounds tested. Compared to estrogenic compounds known in the art, the benefit of serum cholesterol reduction without adversely affecting uterine weight is quite rare and desirable.

As is expressed in the data below, estrogenicity also was assessed by evaluating the adverse response of eosinophil infiltration into the uterus. The compounds of the instant invention did not cause any increase in the number of eosinophils observed in the stromal layer of ovariectomized rats, while estradiol cause a substantial, expected increase in eosinophil infiltration.

The data presented in Table 1 below reflects the response of 5 to 6 rats per treatment.

TABLE 1

| Compound | Dose mg/kg[a] | Uterine Weight % Increase[b] | Uterine Eosinophil (Vmax)[c] | Serum Cholest. % Decrease[d] |
|---|---|---|---|---|
| $EE_2$[e] | 0.1 | 211.0* | 357.3* | 95.2* |
| Example 3 | 0.1 | 29.3* | 5.4 | 12.0 |
|  | 1 | 26.7* | 6.3 | 35.7* |
|  | 10 | 28.6* | 18.0* | 65.0* |

[a]mg/kg PO
[b]Uterine weight % increase verses ovarietomized controls
[c]Eosinophil peroxidase
[d]Serum cholesterol decrease verses ovarietomized controls
[e]17-a-Ethynyl estradiol
*p < 0.05

In addition to the demonstrated benefits of the compounds of the instant invention, the above data clearly demonstrate that compounds of formula I are not estrogen mimetics. Furthermore, no deleterious toxicological effects (for example, survival numbers) were observed with any treatment.

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, compounds of the instant invention and ethynyl estradiol ($EE_2$) in 20% hydroxypropyl b-cyclodextrin are orally administered to test animals. Results are reported as percent protection relative to ovariectomy.

Ovariectomy of the test animals causes a significant reduction in femur density compared to intact, vehicle treated controls. Orally administered ethynyl estradiol ($EE_2$) prevents this loss, but the risk of uterine stimulation with this treatment is ever-present.

MCF-7 Proliferation Assay

MCF-7 breast adenocarcinoma cells (ATCC HTB 22) were maintained in MEM (minimal essential medium, phenol red-free, Sigma, St. Louis, Mo.) supplemented with 10% fetal bovine serum (FBS) (V/V), L-glutamine (2 mM), sodium pyruvate (1 mM), HEPES {(N-[2-hydroxyethyl] piperazine—N'-[2-ethanesulfonic acid]10 mM}, non-essential amino acids and bovine insulin (1 mg/mL) (maintenance medium). Ten days prior to assay, MCF-7 cells were switched to maintenance medium supplemented with 10% dextran coated charcoal stripped fetal bovine serum (DCC-FBS) assay medium) in place of 10% FBS to deplete internal stores of steroids. MCF-7 cells were removed from maintenance flasks using cell dissociation medium ($Ca^{++}$/$Mg^{++}$ free HBSS (phenol red-free) supplemented with 10 mM HEPES and 2 mM EDTA). Cells were washed twice with assay medium and adjusted to 80,000 cells/mL.

Approximately 100 mL (8,000 cells) were added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control were prepared in assay medium and 50 mL transferred to triplicate microcultures followed by 50 mL assay medium for a final volume of 200 mL. After an additional 48 hours at 37° C. in a 5% $CP_2$ humidified incubator, microcultures were pulsed with tritiated thymidine (1 uCi/well) for 4 hours. Cultures were terminated by freezing at −70° C. for 24 hours followed by thawing and harvesting of microcultures using a Skatron Semiautomatic Cell Harvester. Samples were counted by liquid scintillation using a Wallace BetaPlace b counter. A compound of Example 3 demonstrated an $EC_{50}$ of 100 nM.

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenzo[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

We claim:
1. A compound of formula I:

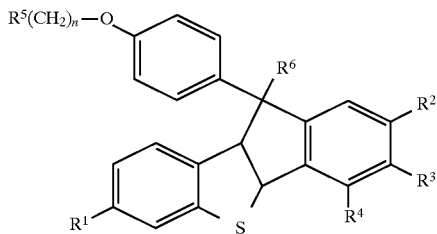

wherein:
$R^1$ is —H, —OH, —X, where —X is a halogen, —O($C_1$–$C_4$ alkyl), —OCO($C_1$–$C_6$ alkyl), —OCO(O)($C_1$–$C_6$ alkyl), —OCOAr, —OCO(O)Ar where Ar is phenyl or substituted phenyl, or —OSO$_2$($C_4$–$C_6$ alkyl);
$R^2$, $R^3$, and $R^4$ are independently —H, —OH, —X, where —X is a halogen, —O($C_1$–$C_4$ alkyl), —OCO($C_1$–$C_6$ alkyl), —OCO(O) ($C_1$–$C_6$ alkyl), —OCOAr, —OCO(O)Ar where Ar is phenyl or substituted phenyl, or —OSO$_2$($C_4$–$C_6$ alkyl);
n is 2 or 3;
$R^5$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; and
$R^6$ is —H, —OH, —X, where —X is a halogen, —CN, —NH$_2$, —NHR$^8$, —NR$^8$R$^9$, where $R^8$ and $R^9$ are both independently $C_1$–$C_6$ alkyl, or $C_1$–$C_6$ alkyl;
or a pharmaceutically acceptable salt or solvate thereof.

2. A compound according to claim 1 wherein n is two.
3. A compound according to claim 1 wherein $R^1$ is methoxy.
4. A compound according to claim 1 wherein $R^2$ is methoxy.
5. A compound according to claim 1 wherein $R^1$ is hydroxy.
6. A compound according to claim 1 wherein $R^2$ is hydroxy.
7. A compound according to claim 1 wherein $R^3$ is hydrogen.
8. A compound according to claim 1 wherein $R^5$ is 1-piperidinyl.
9. A compound according to claim 1 wherein $R^2$ and $R^4$ are both hydrogen.
10. A compound according to claim 1 selected from the group consisting of
10-[4-[2-(1-Piperidinyl)ethoxy]phenyl]-3,7-dimethoxy dihydrobenzo[b]indeno[2,1-d]thiophene;
10-[4-[2-(1-Piperidinyl)ethoxy]phenyl]dihydrobenzo[b] indeno[2,1-d] thiophene;
10-[4-[2-(1-Piperidinyl)ethoxy]phenyl]-3,7-dihydroxy dihydrobenzo[b]indeno[2,1-d]thiophene;
10-[4-[2-(1-Piperidinyl)ethoxy]phenyl]-7-methoxy dihydrobenzo[b]indeno[2,1-d]thiophen-10-ol;
10-[4-[2-(1-Piperidinyl)ethoxy]phenyl]-2,7-dimethoxy dihydrobenzo[b]indeno[2,1-d]thiophen-10-ol;
10-[4-[2-(1-Piperidinyl)ethoxy]phenyl]-7-hydroxy dihydrobenzo[b]indeno[2,1-d]thiophen-10-ol;
10-[4-[2-(1-Piperidinyl)ethoxy]phenyl]-7-methoxy dihydrobenzo[b]indeno[2,1-d]thiophene;
10-[4-[2-(1-Piperidinyl)ethoxy]phenyl]-2,7-dimethoxydihydrobenzo[b]indeno[2,1-d]thiophene;
10-[4-[2-(1-Piperidinyl)ethoxy]phenyl]-7-hydroxy dihydrobenzo[b]indeno[2,1-d]thiophene hydrochloride;
10-[4-[2-(1-Pyrrolidinyl)ethoxy]phenyl]-3,7-dimethoxy dihydrobenzo[b]indeno[2,1-d]thiophene;
10-[4-[2-(1-Pyrrolidinyl)ethoxy]phenyl]dihydrobenzo[b] indeno[2,1-d]thiophene;
10-[4-[2-(1-Pyrrolidinyl)ethoxy]phenyl]-3,7-dihydroxy dihydrobenzo[b]indeno[2,1-d]thiophene;
10-[4-[2-(1-Pyrrolidinyl)ethoxy]phenyl]-7-methoxy dihydrobenzo[b]indeno[2,1-d]thiophen-10-ol;
10-[4-[2-(1-Pyrrolidinyl)ethoxy]phenyl]-2,7-dimethoxy dihydrobenzo[b]indeno[2,1-d]thiophen-10-ol;
10-[4-[2-(1-Pyrrolidinyl)ethoxy]phenyl]-7-hydroxy dihydrobenzo[b]indeno[2,1-d]thiophen-10-ol;
10-[4-[2-(1-Pyrrolidinyl)ethoxy]phenyl]-7-methoxy dihydrobenzo[b]indeno[2,1-d]thiophene;
10-[4-[2-(1-Pyrrolidinyl)ethoxy]phenyl]-2,7-dimethoxydihydrobenzo[b]indeno[2,1-d]thiophene; and
10-[4-[2-(1-Pyrrolidinyl)ethoxy]phenyl]-7-hydroxy dihydrobenzo[b]indeno[2,1-d]thiophene hydrochloride.

11. A method of inhibiting bone loss or bone resorption which comprises administering to a patient in need thereof an effective amount of a compound of claim 1.

12. A method according to claim 11, wherein said bone loss or bone resorption is due to menopause or ovariectomy.

13. A method of lowering serum cholesterol levels which comprises administering to a patient in need thereof an effective amount of a compound of claim 1.

14. A method of inhibiting estrogen-dependent cancer which comprises administering to a patient in need thereof an effective amount of a compound of claim 1.

15. A method according to claim 14 wherein said estrogen-dependent cancer is breast cancer.

16. A method according to 14 wherein said estrogen-dependent cancer is uterine cancer.

17. A compound of formula XIII

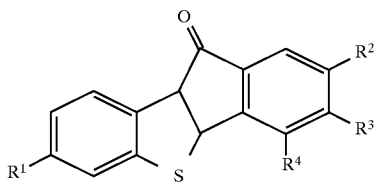

wherein:

$R^1$ is —H, —OH, —O($C_1$–$C_4$ alkyl), —OCO($C_1$–$C_6$ alkyl), —OCO(O) ($C_1$–$C_6$ alkyl), —OCOAr, —OCO(O)Ar where Ar is phenyl or substituted phenyl, or —OSO$_2$($C_4$–$C_6$ alkyl); and $R^2$, $R^3$, and $R^4$ are independently —H, —OH, —X, where —X is a halogen, —O($C_1$–$C_4$ alkyl), —OCO($C_1$–$C_6$ alkyl), —OCO(O) ($C_1$–$C_6$ alkyl), —OCOAr, —OCO(O)Ar where Ar is phenyl or substituted phenyl, or —OSO$_2$($C_4$–$C_6$ alkyl).

18. A process for preparing a compound of formula IIIa

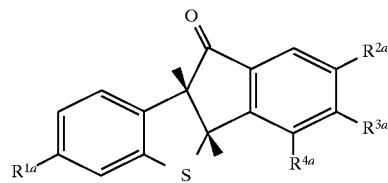

which comprises:

(a) cyclizing a compound of formula XII

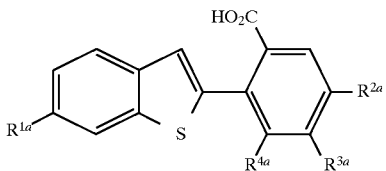

in the presence of a Friedel-Crafts alkylating agent and an acid catalyst;

wherein:

$R^{1a}$ is —H or —OR$^7$, where $R^7$ is a hydroxy protecting group;

$R^{2a}$, $R^{3a}$, and $R^{4a}$ are independently —H, —OR$^7$, where $R^7$ is a hydroxy protecting group, —F, —Cl, and $C_1$–$C_4$ alkyl;

$R^5$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; and n is 2 or 3;

(b) followed by reduction.

* * * * *